United States Patent [19]

Kinoshita

[11] 4,279,247
[45] Jul. 21, 1981

[54] ENDOSCOPE HAVING A PLURALITY OF OPTICAL SYSTEMS EACH PROVIDED WITH AN IDENTIFICATION MARK ELEMENT

[75] Inventor: Kunio Kinoshita, Hachioji, Japan

[73] Assignee: Olympus Optical Co., Ltd., Tokyo, Japan

[21] Appl. No.: 59,333

[22] Filed: Jul. 20, 1979

[30] Foreign Application Priority Data

Jul. 27, 1978 [JP] Japan .................. 53/103250

[51] Int. Cl.³ .............................. A61B 1/06
[52] U.S. Cl. ...................... 128/6; 350/96.26
[58] Field of Search ...................... 128/3–8; 350/96.26, 254, 39; 356/241; 354/105, 62

[56] References Cited

U.S. PATENT DOCUMENTS

| | | | |
|---|---|---|---|
| 3,525,561 | 8/1970 | Takahashi | 128/4 |
| 3,595,220 | 7/1971 | Kawahara | 128/6 |
| 3,703,169 | 11/1972 | Ouchi | 128/6 |
| 3,730,632 | 5/1973 | Chikama | 128/6 X |
| 3,817,635 | 6/1974 | Kawahara | 128/6 |
| 3,866,602 | 2/1975 | Furihata | 128/6 |
| 3,889,662 | 6/1975 | Mitsui | 128/6 |
| 4,153,333 | 5/1979 | Harada et al. | 350/96.26 |

FOREIGN PATENT DOCUMENTS

| | | | |
|---|---|---|---|
| 1946693 | 8/1970 | Fed. Rep. of Germany | 350/96.20 |
| 37-31393 | 11/1962 | Japan | 128/6 |
| 49-134191 | 12/1974 | Japan | . |
| 52-23975 | 5/1977 | Japan | . |

*Primary Examiner*—Kyle L. Howell
*Assistant Examiner*—Arthur S. Rose

[57] ABSTRACT

An endoscope having a plurality of observation optical systems comprises an elongated sheath, a distal end section connected to one end of the sheath, an operation section connected to the other end of the sheath, a plurality of optical fiber bundles extending through the sheath, an ocular section provided at the operation section, an observation optical system selecting section provided between the operation section and the ocular section and including a rotary member which holds the proximal ends of the optical fiber bundles and which is rotated to selectively connected one of the bundles optically to the ocular section, and identification mark elements in the fields of view of the optical fiber bundles. Each mark element lies in the field of view of the ocular section while the corresponding optical fiber bundle is optically connected to the ocular section, thus identifying the observation optical system used.

9 Claims, 10 Drawing Figures

ENDOSCOPE HAVING A PLURALITY OF OPTICAL SYSTEMS EACH PROVIDED WITH AN IDENTIFICATION MARK ELEMENT

BACKGROUND OF THE INVENTION

This invention relates to an endoscope having a plurality of observation optical systems, and more particularly to an endoscope having a plurality of optical systems each provided with an identification mark element which lies in view of an ocular section of the endoscope while the optical system is used.

An endoscope has been known which is provided with two or more optical systems, for example, a front viewing optical system and a lateral viewing optical system so as to be selectively used. When one of them is used, its proximal end faces the ocular section of the endoscope. Since the proximal ends of the optical systems, which appear in the field of view of the ocular section, are identical and can hardly be distinguished from one another, an operator must previously ascertain which optical system is used. When the operator forgets during the observation of a body cavity which observation optical system is actually used, or it has become impossible to judge which optical system is used at the present moment due to their repeated interchanges, the difficulties arise in operating the endoscope safely and reliably.

SUMMARY OF THE INVENTION

An object of this invention is to provide an endoscope having a plurality of observation optical systems, each provided with an identification mark element which lies in the field of view of an ocular section of the endoscope while the corresponding optical system is used so as to identify the optical system, whereby the endoscope is operated safely and correctly.

An endoscope according to this invention comprises an elongated sheath, a distal end section connected to one end of the sheath, an operation section connected to the other end of the sheath, a plurality of observation optical fiber bundles extending through the sheath, an ocular section provided on the operation section, an optical system selecting section provided between the operation section and the ocular section and including an alignment member which holds the proximal ends of the observation optical fiber bundles and which is moved to selectively align one of the observation optical fiber bundles with the ocular section, and identification mark elements having different configurations from one another and disposed in fields of view of the corresponding observation optical fiber bundles.

BRIEF DESCRIPTION OF THE DRAWING

This invention can be fully understood from the following detailed description with reference to the accompanying drawings.

DESCRIPTION OF THE PREFERRED EMBODIMENTS

Figure 1:
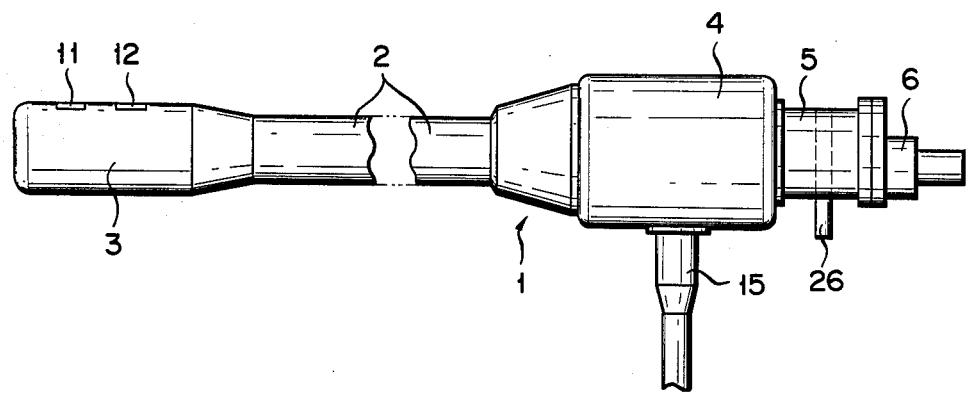
FIG. 1 is a side view of an endoscope embodying this invention.

As shown in FIG. 1, the endoscope 1 comprises a flexible elongated sheath 2, a rigid distal end section 3 connected to the distal end of the sheath 2 and an operation section 4 connected to the proximal end of the sheath 2. An observation optical system selecting section 5 is provided on the proximal end of the operation section 4, and an ocular section 6 is fixed to the proximal end of the observation optical system selecting section 5.

Figure 2:
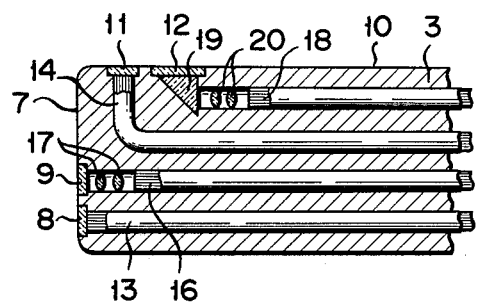
FIG. 2 is a longitudinal cross-sectional view of the distal end section of the endoscope shown in FIG. 1.

As illustrated in FIG. 2, the front face 7 of the distal end section 3 has a front viewing illumination window 8 and a front viewing observation window 9 positioned close to the window 8. The periphery 10 of the distal end section 3 has a lateral viewing illumination window 11 and a lateral viewing observation window 12 positioned close to the window 11. An illumination optical fiber bundle 13 which guides illumination light for a front viewing purpose and an illumination optical fiber bundle 14 which guides illumination light for a lateral viewing purpose extend through the sheath 2 and the distal end section 3. The optical fiber bundle 13 is optically connected at one end to the front viewing illumination window 9 and at the other end to a light source (not shown) through a connection tube 15 (FIG. 1) which protrudes from a lateral side of the operation section 4. Similarly, the optical fiber bundle 14 is optically connected at one end to the lateral viewing illumination window 11 and at the other end to the light source through the connection tube 15.

An observation optical fiber bundle 16 extends through the distal end section 3, sheath 2 and operation section 4, and has its distal end optically connected to the window 9 via lenses 17. Another observation optical fiber bundle 18 extends through the distal end section 3, sheath 2 and operation section 4, and has its distal end optically connected to the window 12 via a Porro prism 19 and lenses 20 which are provided within the distal end section 3.

Figure 3:
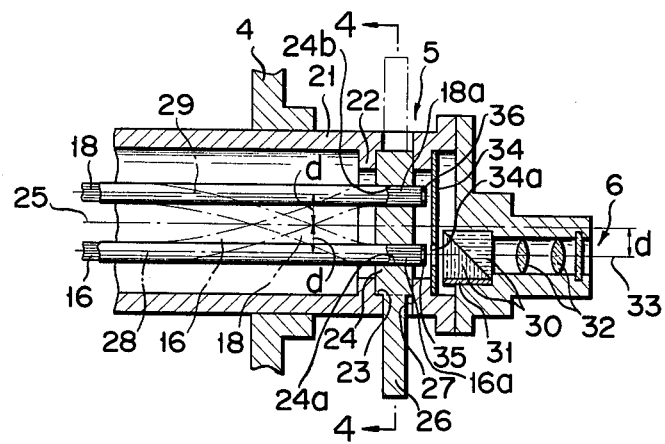
FIG. 3 is a longitudinal cross-sectional view of the operation section, ocular section and optical system selecting section of the endoscope shown in FIG. 1.
Figure 4:
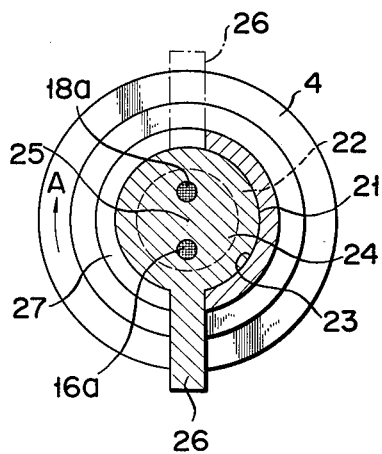
FIG. 4 is a cross-sectional view taken along line 4—4 in FIG. 3.

As shown in FIGS. 3 and 4, the optical system selecting section 5 comprises a hollow cylindrical housing 21 which is partly inserted in the operation section 4. The housing 21 has a thick portion 22 at its proximal end portion. In the inner surface of the thick portion 22, an annular groove 23 is formed. The annular groove 23 receives the peripheral edge portion of a disc-shaped rotary member 24, which is rotatable about the axis 25 of the hollow cylindrical housing 21. From the outer periphery of the rotary member 24, a handle 26 extends in the radial direction of the housing 21 and protrudes outside the housing 21 through a semicircular guide slit 27 formed in the thick portion 22 of the housing 21. The rotary member 24 can therefore be rotated through 180° by moving the handle 26 between two positions which are indicated by solid line and dotted line in FIGS. 3 and 4. The rotary member 24 has two axial through holes 24a, 24b which are arranged diametrically opposite to each other. The proximal end 16a of the optical fiber bundle 16 is held in the hole 24a, and the proximal end 18a of the optical fiber bundle 18 is held in the hole 24b. The central axes 28, 29 of the bundles 16, 18 are separated by a distance d from the central axis 25 of the rotary member 24.

The ocular section 6 has a pair of right angle prisms 30, a photo-electric transducer element 31 and lenses 32. Its optical axis 33 can be aligned alternatively with the axis 28 of the proximal end 16a of the optical fiber bundle 16 or the axis 29 of the proximal end 18a of the optical fiber bundle 18.

In FIG. 3, the axis 28 aligns with the optical axis 33. A diaphragm 34 is mounted in the thick portion 22 of the housing 21 in parallel to the rotary member 24. The diaphragm 34 faces the proximal ends 16a and 18a of the optical fiber bundles 16 and 18. It has an opening 34a which aligns with the optical axis 33 of the ocular section 6 and which has substantially the same diameter as the field of view of the optical fiber bundles 16 and 18. When the handle 26 is rotated in the direction of arrow A in FIG. 4, the rotary member 24 rotates by 180° to bring the proximal end 18a of the bundle 18 before the opening 34a, thereby to align its axis 29 with the optical axis 33 of the ocular section 6.

The lenses 20 and the optical fiber bundle 16 constitute an observation optical system for the front viewing purpose, and the Porro prism 19, the lenses 20 and the optical fiber bundle 18 constitute an observation optical system for the lateral viewing purpose.

An identification mask 35 is mounted on the proximal end 16a of the optical fiber bundle 16, and an identification mask 36, on the proximal end 18a of the optical fiber bundle 18.

Figure 5:
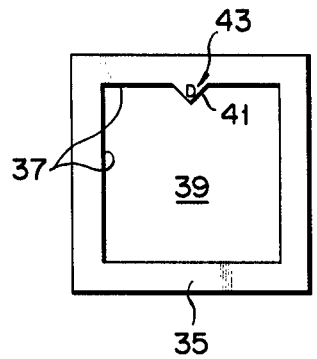
FIG. 5 is a front view of an identification mask for a front viewing optical system.
Figure 6:
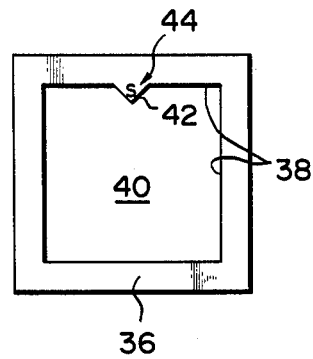
FIG. 6 is a front view of an identification mask for a lateral viewing optical system.

As shown in FIG. 5, the mask 35 is a square plate having a square opening 39, which is defined by four inner edges 37 and is an large as the field of view of the optical fiber bundle 16. On one of the edges 37 is provided a V-shaped projection 41 extending into the opening 39. An identification mark 43 consisted of a letter D is shown on the projection 41. Similarly, as shown in FIG. 6, the mask 36 is a square plate having a square opening 40 which is defined by four inner edges 38 and is as large as the field of view of the optical fiber bundle 18. One of the edges 38 has a V-shaped projection 42 extending into the opening 40. An identification mark 44 consisted of a letter S is shown on the projection 42. In case the masks 35 and 36 are not transparent, that is, opaque, the marks 43 and 44 are transparent. On the other hand, if the masks 35 and 36 are transparent, the marks 43 and 44 are not transparent, that is, opaque.

Figure 7:
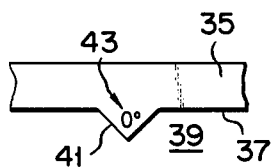
FIG. 7 is a front view of main part of another identification mask for a front viewing optical system.
Figure 8:
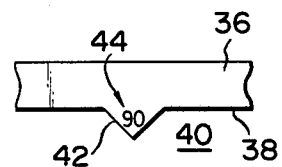
FIG. 8 is a front view of main part of another identification mask for a lateral viewing optical system.

The identification marks 43 and 44 may be figures, for example "0°" and "90" as illustrated in FIG. 7 and FIG. 8, in place of the letters "D" and "S" as shown in FIGS. 5 and 6.

Figure 9:
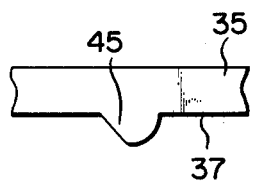
FIG. 9 is a front view of a main part of still another identification mask for a front viewing optical system.
Figure 10:
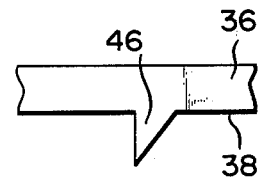
FIG. 10 is a front view of a main part of still another identification mask for a lateral viewing optical system.

Further, the projection may be used as identification marks, as shown in FIGS. 9 and 10. One of the inner edges 37 of the mask 35 has a sector-shaped projection 45 as shown in FIG. 9, and one of the inner edges 38 of the mask 36 has a sawtooth-shaped projection 46 (that is, a projection defined by a side adjacent to the right angle and the oblique side of a right triangle). In this case, the sector-shaped projection 45 identifies the front viewing observation optical system, while the sawtooth-shaped projection 46, the lateral viewing observation optical system. However, they can be interchanged.

In operation, as long as the handle 26 of the rotary member 24 remains at the position indicated by solid line in FIGS. 3 and 4, the axis of the proximal end 16a of the optical fiber bundle 16 for front view observation is aligned with the optical axis 33 of the ocular section 6. In this case, the mask 35 appears in the field of view of the ocular section 6. From the mark 43 ("D" or "0°") or the sector-shaped projection 45 in the field of view of the ocular section 6, the operator understands that he is observing the interior of a body cavity through the front vewing optical system. When the handle 26 is rotated to the position indicated by the dotted line in FIGS. 3 and 4, the axis 29 of the proximal end 18a of the optical fiber bundle 18 for lateral view observation aligns with the optical axis 33 of the ocular section 6. As a result, the mask 36 appears in the field of view of the ocular section 6. From the mark 44 ("S" or "90") or the projection 46, the operator understands that he is observing the interior of the body cavity through the lateral viewing optical system.

The operator need not leave his eye off the ocular section 6 in order to make sure which observation optical system is used. Therefore, the operator does not misunderstand through which observation optical system he is observing the body cavity, and he knows how to operate the endoscope. Thus the observation of the body cavity can be quickly carried out, and the body cavity is treated safely.

The mark 43 is "D" or "0°", and the mark 44 is "S" or "90" as illustrated in FIGS. 5 to 8. They are not symmetrical letter or figure. The projections 45 and 46 are not symmetrical, either, as shown in FIGS. 9 and 10. For this reason, the front side of a slide prepared by endoscope photography can be distinguished from its reverse side by checking the image of the mark in the field of view of the ocular section, thereby to ensure an exact examination of a body cavity.

Instead of the rotary member 24, there may be used a plate-like member which mounts the proximal ends 16a, 18a of the observation optical fiber bundles 16, 18 in a spaced relation from each other such that the ends 16a, 18a are selectively aligned with the optical axis 33 of the ocular section 6 by moving the plate-like member perpendicularly to the axis 33.

What is claimed is:

1. An endoscope having observation optical systems comprising:
    an elongated sheath having two ends;
    a distal end section connected to one of said ends of the sheath;
    an operation section having two ends, one end being connected to the other end of the sheath;
    two elongated observation optical systems extending through the sheath and each having two ends, one end being optically connected to the exterior of the endoscope at the distal end section, each of said observation optical systems having a field of view, one of said two observation optical systems being a front viewing observation optical system, and said other observation optical system being a lateral viewing optical system;
    an ocular section disposed at the other end of the operation section and having an optical axis;
    a rotatable observation optical system selecting section disposed between the operation section and the ocular section for selectively aligning the other end of the respective observation optical system with the optical axis of the ocular section; and identification mark elements each disposed in the field of view of the corresponding observation optical system and having configurations so different from each other as to identify the corresponding observation optical system when viewed through the ocular section.

2. The endoscope according to claim 1, wherein said observation optical systems are each provided on the other end thereof with a mask having an opening substantially matching the field of view of the corresponding observation optical system and also having a projection extending into the opening, and said identification mark elements being provided on the corresponding projection.

3. The endoscope according to claim 2, wherein each of said identification mark elements has a different configuration when reversed.

4. The endoscope according to claim 3, wherein said mask is opaque, and said identification mark elements are transparent.

5. The endoscope according to claim 3, wherein said mask is transparent, and said identification marks are opaque.

6. The endoscope according to claim 3, wherein said projections are formed asymmetric.

7. The endoscope according to claim 6, wherein said projection of said identification mark element on one of said two observation optical systems has the shape of a sector, and said projection of said identification mark element on the other of said two observation optical systems has the shape of a saw-tooth.

8. The endoscope according to claim 3, wherein said identification mark element on said front viewing observation optical system has the shape of a letter D, and said identification mark element on said lateral viewing optical system has the shape of a letter S.

9. The endoscope according to claim 3, wherein said identification mark element on said front viewing observation optical system has the shape of a sign 0°, and said identification mark element on said lateral viewing observation optical system has the shape of a figure 90.

* * * * *